United States Patent
Ryu et al.

(10) Patent No.: US 7,715,915 B1
(45) Date of Patent: May 11, 2010

(54) NEUROSTIMULATION AND NEUROSENSING TECHNIQUES TO OPTIMIZE ATRIAL ANTI-TACHYCARDIA PACING FOR PREVENTION OF ATRIAL TACHYARRHYTHMIAS

(75) Inventors: Kyungmoo Ryu, Palmdale, CA (US); Jong Gill, Valencia, CA (US); Taraneh Ghaffari Farazi, San Jose, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 341 days.

(21) Appl. No.: 11/615,497

(22) Filed: Dec. 22, 2006

(51) Int. Cl.
*A61N 1/00* (2006.01)

(52) U.S. Cl. ............................................. 607/9; 607/14
(58) Field of Classification Search .............. 607/1–28
See application file for complete search history.

(56) References Cited

U.S. PATENT DOCUMENTS

| | | | |
|---|---|---|---|
| 5,203,326 A | 4/1993 | Collins | |
| 5,243,980 A | 9/1993 | Mehra | |
| 5,334,221 A | 8/1994 | Bardy | |
| 5,397,342 A | 3/1995 | Heil, Jr. et al. | |
| 5,658,318 A | 8/1997 | Stroetmann et al. | |
| 5,690,681 A | 11/1997 | Geddes et al. | |
| 5,916,239 A | 6/1999 | Geddes et al. | |
| 5,951,593 A * | 9/1999 | Lu et al. | 607/14 |
| 6,266,564 B1 | 7/2001 | Hill et al. | |
| 6,272,377 B1 * | 8/2001 | Sweeney et al. | 600/515 |
| 6,473,644 B1 | 10/2002 | Terry, Jr. et al. | |
| 6,922,585 B2 | 7/2005 | Zhou et al. | |
| 6,934,583 B2 | 8/2005 | Weinberg et al. | |
| 7,020,530 B1 * | 3/2006 | Ideker et al. | 607/122 |
| 2003/0078623 A1 | 4/2003 | Weinberg et al. | |
| 2003/0191403 A1 | 10/2003 | Zhou et al. | |
| 2004/0199210 A1 | 10/2004 | Shelchuk | |
| 2005/0187586 A1 | 8/2005 | David et al. | |
| 2005/0261672 A1 | 11/2005 | Deem et al. | |
| 2005/0261741 A1 | 11/2005 | Libbus et al. | |
| 2007/0073179 A1 | 3/2007 | Afonso et al. | |

FOREIGN PATENT DOCUMENTS

| | | |
|---|---|---|
| EP | 0547734 A2 | 6/1993 |
| EP | 0547734 A3 | 6/1993 |
| EP | 0547734 B1 | 6/1993 |
| EP | 0721786 B1 | 7/1996 |

OTHER PUBLICATIONS

Bailin, Steven J. et al., "Prevention of Chronic Atrial Fibrillation by Pacing in the Region of Bachmann's Bundle: Results of a Multicenter Randomized Trial," J Cardiovasc Electrophysiol, vol. 12, pp. 912-917, Aug. 2001.

(Continued)

*Primary Examiner*—Scott M Getzow

(57) ABSTRACT

Implantable systems, and method for use therewith, are provided that take advantage of various neuromodulation and neurosensing techniques for either preventing atrial fibrillation (AF) or terminating AF. Specific embodiments, as will be described below, are for use with an implantable device that include one or more atrial electrode for sensing atrial fibrillation (AF) and/or delivering AATP and one or more electrode for monitoring and/or stimulating atrial vagal fat pads.

10 Claims, 7 Drawing Sheets

OTHER PUBLICATIONS

Carlson, Mark D. MD, MA et al., "Selective Stimulation of Parasympathetic Nerve Fibers to the Human Sinoatrial Node," Circulation, 1992;85: 1311-1317.

Chiou, Chuen-Wang MD et al., "Efferent Vagal Innervation of the Canine Atria and Sinus and Atrioventricular Nodes—The Third Fat Pad," Circulation, 1997;95: 2573-2584.

Davis, Zev et al., "Aortic Fat Pad Destruction and Post Operative Atrial Fibrillation," Cardiac Electrophysiology Review, 2003;7: 185-188.

Israel, Carsten W., "Pace—Termination and Pacing for Prevention of Atrial Tachyarrhythmias: Results from a Multicenter Study with an Implantable Device for Atrial Therapy," JCardiovasc Electrophysiol, vol. 12, pp. 1121-1128, Oct. 2001.

Kilgore, K.L. et al., "Nerve conduction block utilising high-frequency alternating current," Med. Biol. Eng. Comput., 2004, 42, 394-406.

Lockwood, Deborah J. MD et al., "Ablation of Epicardial Autonomic Ganglionated Plexi during Minimally Invasive Surgical Ablation of Atrial Fibrillation," Heart Rhythm, vol. 3(5), pp. S92-S93 (Abstract-AB44-6), 2006.

Padeletti, Luigi MD et al., "Combined Efficacy of Atrial Septal Lead Placement and Atrial Pacing Algorithms for Prevention of Paroxysmal Atrial Tachyarrhythmia," J Cardiovasc Electrophysiol, vol. 14, pp. 1189-1195, Nov. 2003.

Saksena, Sanjeev MD et al., "Prevention of Recurrent Atrial Fibrillation With Chronic Dual-Site Right Atrial Pacing," J Am Coll Cardiol 1996;28: 687-94.

Scherlag, Benjamin J. et al., "Electrical Stimulation to Identify Neural Elements on the Heart: Their Role in Atrial Fibrillation," Journal of Interventional Cardiac Electrophysiology 13, 37-42, 2005.

Yu, Wen-Chung MD et al., "Effects of Different Atrial Pacing Modes on Atrial Electrophysiology—Implicating the Mechanism of Biatrial Pacing in Prevention of Atrial Fibrillation," Circulation, 1997;96: 2992-2996.

Nakagawak, Hiroshi MD et al., "Comparison of Areas of Fractionated Atrial Potentials and Location of Autonomic Ganglionated Plexi Between Patients with Paroxysmal, Persistent and Permanent Atrial Fibrillation," Heart Rhythm, vol. 3, No. 5 (Abstract-AB3-5), 2006.

NonFinal Office Action, mailed Jan. 8, 2009: Related U.S. Appl. No. 11/615,497.

Sinha, Sitabhra et al., "Spatiotemporal Dynamics of Pacing in Models of Anatomical Reentry," Engineering Medicine and Biology Society. 2001; Proceeding of the 23rd Annual Intern'l Conference of the IEEE;1:70-73.

NonFinal Office Action, mailed Jul. 9, 2009: Related U.S. Appl. No. 11/615,497.

Po, Sunny et al. "Experimental model for the paroxysmal atrial fibrillation arising at the pulmonary vein-junctions," Heart Rhythm. 2006;3(2):201-208.

* cited by examiner

NEUROSTIMULATION AND NEUROSENSING TECHNIQUES TO OPTIMIZE ATRIAL ANTI-TACHYCARDIA PACING FOR PREVENTION OF ATRIAL TACHYARRHYTHMIAS

RELATED APPLICATION

The present application is related to commonly invented and commonly assigned U.S. patent application Ser. No. 11/615,488, entitled NEUROSTIMULATION AND NEUROSENSING TECHNIQUES TO OPTIMIZE ATRIAL ANTI-TACHYCARDIA PACING FOR TERMINATION OF ATRIAL TACHYARRHYTHMIAS, filed the same day as the present application, which is incorporated herein by reference.

FIELD OF THE INVENTION

The present invention relates generally to programmable implantable cardiac devices, and particularly those devices that stimulate vagal nerve fibers innervating fat pads in response to a variety of conditions including atrial fibrillation, atrial arrhythmia and vagal fiber irregularity and/or carry out atrial anti-tachycardia pacing.

BACKGROUND

The heart is a pump which pumps blood throughout the body. It consists of four chambers, including a left atrium, a right atrium, a left ventricle and a right ventricle. In order for the heart to efficiently perform its function as a pump, the atrial muscles and ventricular muscles should contract in a proper sequence and in a timed relationship.

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A typical healthy adult heart can beat at a rate of 60-70 beats per minute (bpm) while at rest, and can increase its rate to 140-180 bpm when the adult is engaging in strenuous physical exercise, or undergoing other physiologic stress.

The healthy heart controls its rhythm from its sino-atrial (SA) node, located in the upper portion of the right atrium. The SA node generates an electrical impulse at a rate commonly referred to as the "sinus" rate. This impulse is delivered to the atrial tissue when the atria are to contract, and, after a suitable delay, propagates to the ventricular tissue when the ventricles are to contract.

When the atria contract, a detectable electrical signal referred to as a P-wave is generated. When the ventricles contract, a detectable electrical signal referred to as the QRS complex (also referred to simply as an "R-wave") is generated, as a result of the depolarization of the ventricles. The R-wave is much larger than the P-wave, principally because the ventricular muscle tissue is much more massive than the atrial muscle tissue. The atrial muscle tissue need only produce a contraction sufficient to move the blood a very short distance, from the respective atrium to its corresponding ventricle. In contrast, the ventricular muscle tissue must produce a contraction sufficient to push the blood over a longer distance (e.g., through the complete circulatory system of the entire body).

It is the function of a pacemaker to provide electrical stimulation pulses to the appropriate chamber(s) of the heart (atria and/or ventricles) in the event the heart is unable to beat on its own (e.g., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is often referred to as the "escape interval"), then a stimulation pulse is generated at the conclusion of this prescribed period of time and delivered to the appropriate heart chamber via a pacemaker lead.

Modern programmable pacemakers are generally of two types: (1) single chamber pacemakers, and (2) dual-chamber pacemakers. In a single chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

Atrial fibrillation (AF) is a characterized by an abnormal heart rhythm in which the atria, or upper chambers of the heart, 'quiver' chaotically and the ventricles beat irregularly, where the resulting heartbeat is completely irregular. In AF, the atrial muscles contract very quickly and irregularly; while the ventricles beat irregularly but not as fast as the atria. When the atria fibrillate, blood that is not completely pumped out can pool and form a clot, which can lead to a stroke if the clot is carried by the blood flow to the brain. According to the American Heart Association, AF is the most common chronic arrhythmia, afflicting nearly 2 million Americans. The prevalence of AF increases with age and is slightly more common in men than in women. AF is responsible for about 15% of strokes. Often, AF begins with short episodes of palpitations or a fluttering sensation in the chest. Over time, there is a tendency for these episodes to become longer. Once AF has been initiated, the atria undergo a process known as 'remodeling'. AF-induced atrial remodeling causes both structural and electrical changes. AF is usually diagnosed through electrocardiography (ECGs), an exercise stress test, a 24-hour Holter ECG monitor, or a telephone cardiac monitor. AF is usually treated with medications and/or electrical shock (cardio version). In some cases, removal of a small portion of the heart (ablation), implantation of a pacemaker or a cardioverter defibrillator is required.

Atrial anti-tachycardia pacing (AATP) is a standard treatment option to terminate most re-entrant tachycardia. Although AATP is very effective on atrial flutter termination (with success in terminating atrial flutter in >80% of cases), AATP is very ineffective on atrial fibrillation (AF) termination (with success in terminating AF in <20% of cases). Recent studies have demonstrated that dual-site right atrial pacing decreases the recurrence of AF and that dual-site bi-atrial pacing decreases the inducibility of AF in patients. However, chronic dual-site atrial pacing alone has proven disappointing in long-term clinical trials.

Neurostimulation of atrial fat pads and/or parasympathetic neural inputs to them has been shown to modulate the SA rate, AV conduction, the atrial effective refractory period (AERP), and its homogeneity across both atria. In particular, tonic neural activity of the atrial fat pads leads to shortening of the AERP and increases the heterogeneity of refractoriness throughout the atria. Neurostimulation to the coronary sinus region adjacent to the AV nodal fat pad can be used to achieve AV nodal block using high frequency, narrow pulses. However the stimulation levels required to achieve AV block are so high that patients report "pain". Lower levels of stimulation that are not perceived as painful generally don't produce enough AV slowing to be considered an effective therapy for atrial fibrillation (AF).

SUMMARY

Embodiments of the present invention are directed to methods and devices that take advantage of various neuromodulation and neurosensing techniques for either preventing atrial fibrillation (AF) or terminating AF. Specific embodiments, as will be described below, are for use with an implantable device that include one or more atrial electrode for sensing atrial fibrillation (AF) and/or delivering AATP and one or more electrode for monitoring and/or stimulating atrial vagal fat pads.

In accordance with specific embodiments of the present invention, one or more atrial electrode is monitored for AF, and one or more atrial vagal fat pad is monitored for hyperactivity. In response to detecting AF, one or more atrial electrode is selected for delivering AATP, and at least one atrial vagal fat pad is stimulated, to thereby terminate the AF. The selection of the atrial electrode can be based on the results of the monitoring of the one or more atrial vagal fat pad for hyperactivity. In accordance with specific embodiments, the detection of hyperactivity can also be used to select which atrial vagal fat pad is stimulated.

In accordance with embodiments where at least two atrial vagal fat pads are monitored, the atrial electrode that is selected for delivering AATP can be the one closest to the atrial vagal fat pad having a longest duration of hyperactivity. In other embodiments, the atrial electrode that is selected for delivering AATP is the one closest to the atrial vagal fat pad having a most intense action potential hyperactivity. In still other embodiments, the atrial electrode that is selected for delivering AATP is the one closest to the atrial vagal fat pad with the most irregular hyperactivity. In accordance with certain embodiments, if no hyperactivity is detected, then a default atrial vagal fat pad is stimulated.

In accordance with embodiments where only one atrial vagal fat pad is stimulated, the atrial electrode selected for delivering AATP is the one closest to the stimulated atrial vagal fat pad. If delivery of AATP to that atrial electrode is unsuccessful in terminating the AF, the atrial electrode that is next closest to the stimulated atrial vagal fat pad is selected for delivering AATP.

In accordance with specific embodiments, stimulation of the one or more atrial vagal fat pad coincides approximately in time with delivery of AATP. In other embodiments, stimulation of the one or more atrial vagal fat pad precedes in time delivery of AATP. Where stimulating one or more atrial vagal fat pad precedes delivering AATP, the selection of the atrial electrode for delivering AATP can be based on the AATP site most effected by preceding atrial vagal fat pad stimulation.

In certain embodiments, stimulation of the one or more atrial vagal fat pad is approximately synchronous in time with delivery of AATP. It can also be that the stimulation of the one or more atrial vagal fat pads triggers the delivery of AATP.

In certain embodiment, two or more atrial vagal fat pads are stimulated approximately simultaneously in time. Alternatively, two or more atrial vagal fat pads are stimulated sequentially.

The above described embodiments relate to terminating AF after it had been detected. The following embodiments are relating to preventing AF before it occurs. If one of the following embodiments are unsuccessful in preventing AF, then one of the above described embodiments can be used to terminate the AF.

In accordance with certain embodiments, an implantable device monitors for imminent AF. Then, in response to predicting imminent AF, one or more atrial vagal fat pad is stimulated to inhibit atrial vagal fat pad activation, to thereby prevent AF.

There are various ways in which the implantable device can predict an imminent AF. For example, the device can monitor for premature atrial contractions (PACs), and predict whether AF is imminent based on detected PACs. Alternatively, or additionally, the device can monitor at least one atrial vagal fat pad for hyperactivity, and predict whether AF is imminent based on whether atrial vagal fat pad hyperactivity is detected.

In accordance with specific embodiments, in order to inhibit atrial vagal fat pad activation, one or more atrial vagal fat pad is stimulated continuously for between at least 1 minute and approximately 90 minutes.

In accordance with specific embodiments, biphasic stimulation of the one or more atrial vagal fat pad is used to inhibit atrial vagal fat pad activation.

In certain embodiments, constant current pacing is used to inhibit atrial vagal fat pad activation.

In various embodiments, a sinusoidal voltage waveform is administered to inhibit atrial vagal fat pad activation. In various embodiments, the frequency of the pulsed waveform is between approximately 1 kHz and approximately 20 kHz.

In certain embodiments, the pulse width is modulated to inhibit atrial vagal fat pad activation.

In certain embodiments, the inhibitory stimulation pulse width is between approximately 2 millisecond and 10 millisecond to inhibit atrial vagal fat pad activation.

In accordance with other embodiments of the present invention, rather than applying inhibitory stimulation to inhibit atrial vagal fat pad activation, excitatory stimulation is delivered to deplete atrial vagal fat pad neurotransmitter release and thereby inhibit AF.

In various embodiments that utilize high frequency pulses, the frequency of the excitatory stimulation can be between approximately 60 Hz and 200 Hz. In other embodiments that utilize low frequency pulses, the frequency of the excitatory stimulation can be between approximately 1 Hz and 5 Hz.

In an embodiment of the invention, sub excitatory stimulation is delivered to one or more atrial vagal fat pad to inhibit AF. In these embodiments of the invention, a percentage of the minimum stimulation that is required for excitatory stimulation to effect neurotransmitter release is applied as sub excitatory stimulation. In various embodiments of the present invention, the sub excitatory stimulation is between approximately 85% and approximately 95% of percentage of the minimum excitatory stimulation. Sub excitatory stimulation does not cause the cell to release neurotransmitters, but does change the properties of cells in the region of the fat pads and thereby inhibits AF.

In accordance with other embodiments of the present invention, rather than applying either fat pad inhibitory stimulation alone or fat pad excitatory stimulation alone, the fat pad stimulation can be delivered together with AATP to inhibit AF.

In accordance with specific embodiments, stimulation of the one or more atrial vagal fat pad coincides approximately in time with delivery of AATP. In other embodiments, stimulation of the one or more atrial vagal fat pad precedes in time delivery of AATP. Where stimulating one or more atrial vagal fat pad precedes delivering AATP, the selection of the atrial electrode for delivering AATP can be based on the AATP site most effected by preceding atrial vagal fat pad stimulation.

This summary is not intended to be a complete description of, or limit the scope of, the invention. Alternative and additional features, aspects, and objects of the invention can be obtained from a review of the specification, the figures, and the claims.

DETAILED DESCRIPTION

Exemplary ICD

Figure 1A:
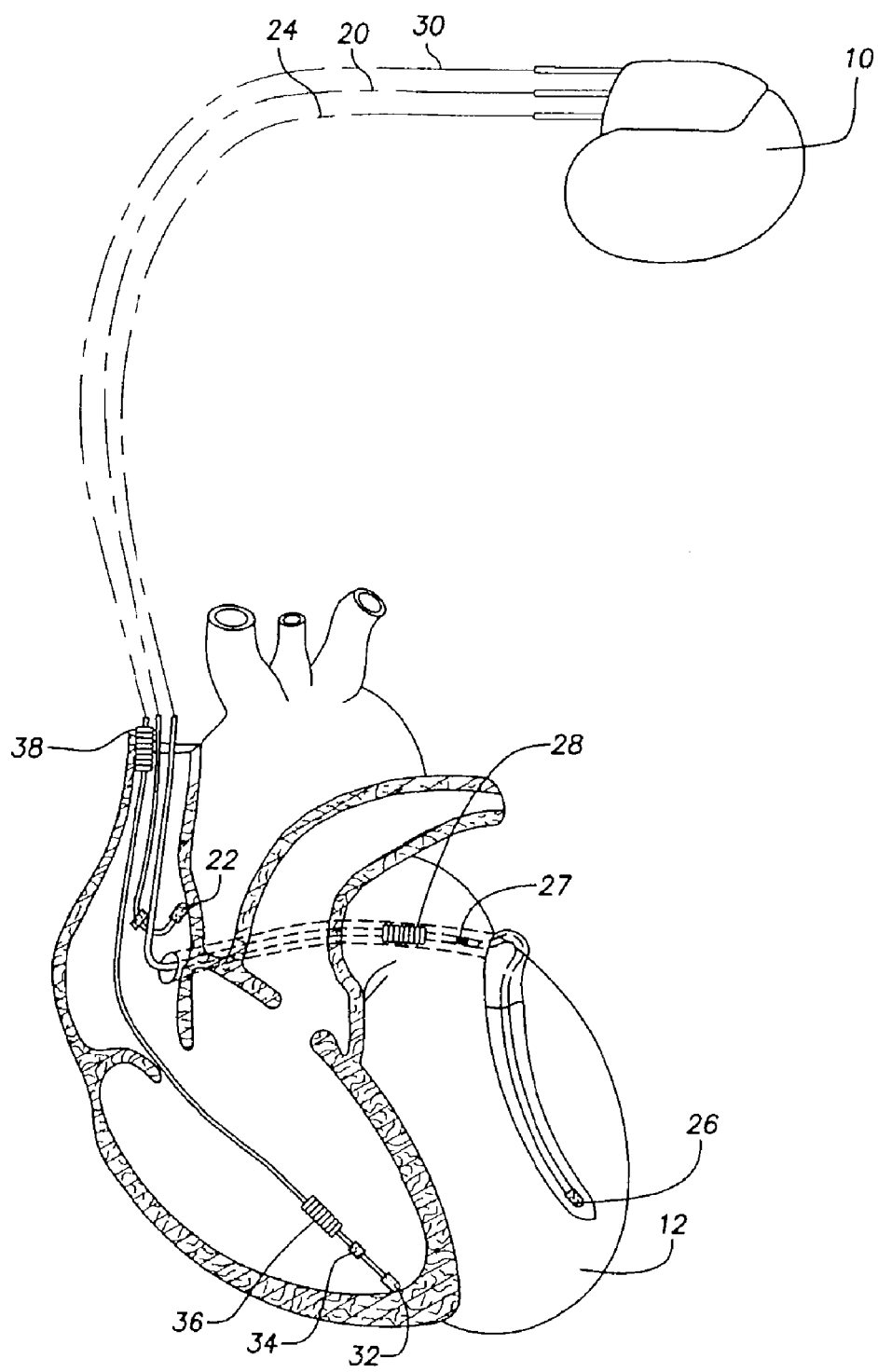
FIG. 1A illustrates an exemplary multi-chamber implantable stimulation device in electrical communication with a patient's heart by way of three or more leads, which are suitable for delivering atrial anti-tachycardia pacing, neural tissue stimulation, multi-chamber pacing, as well as shock therapy (an exemplary ICD includes leads which are suitable for monitoring vagal fiber fat pads for hyperactivity, not shown in FIG. 1)
Figure 2:
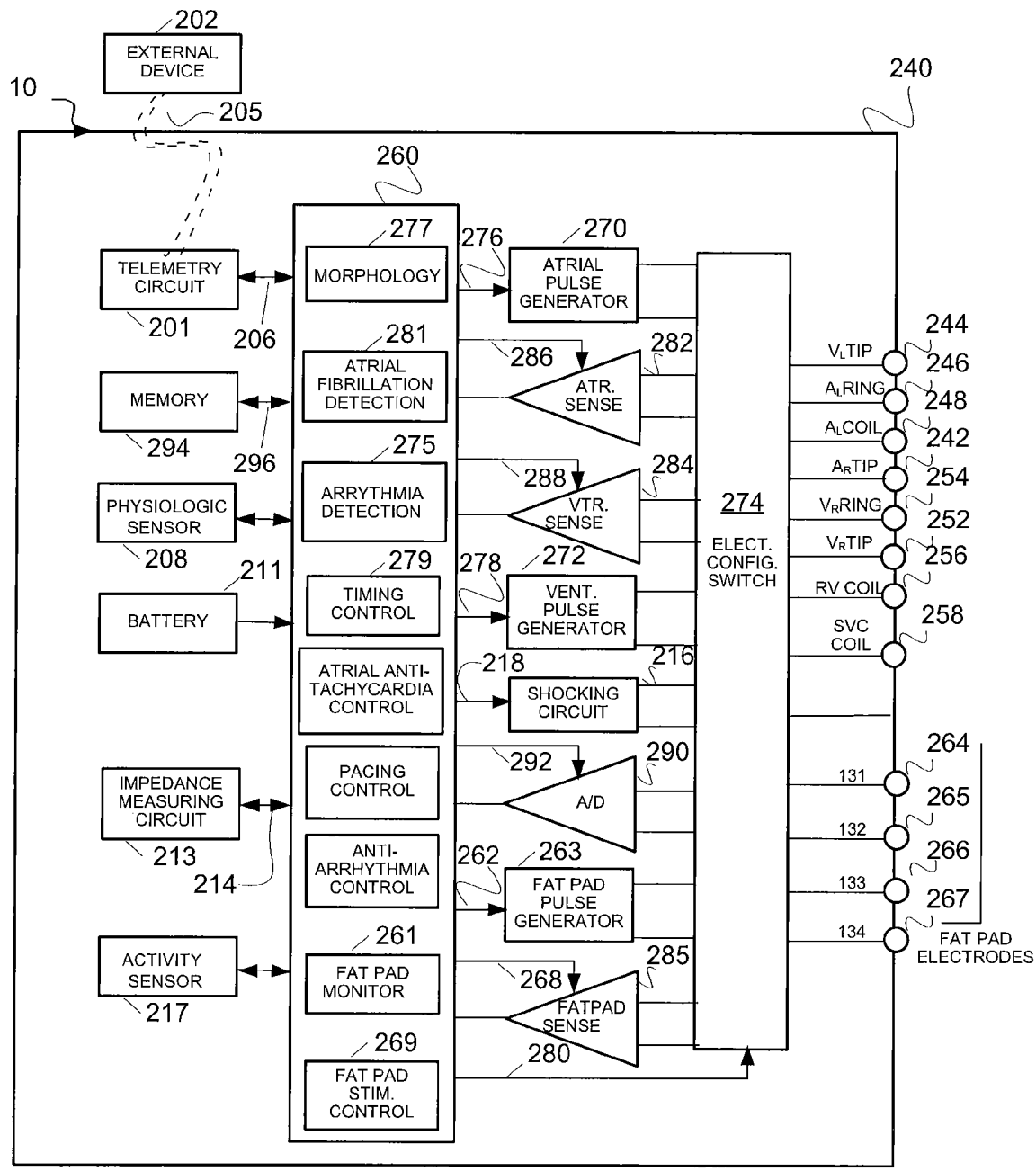
FIG. 2 is a simplified block diagram of the multi-chamber implantable stimulation device of FIG. 1A.

Before describing the invention in detail, it is helpful to describe an example environment in which the invention may be implemented. The present invention is particularly useful in the environment of an implantable cardiac device that can monitor electrical activity of a heart, activity of fat pads located at nerve fiber endings and deliver appropriate electrical therapy, for example, pacing pulses, atrial vagal fat pad stimulation and atrial vagal fat pad neurotransmitter depletion, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIG. 1A and FIG. 2 illustrate such an environment in which embodiments of the present invention can be used.

Referring first to FIG. 1A, an exemplary ICD 10 is shown in electrical communication with a patient's heart 12 by way of three leads, 20, 24 and 30, suitable for delivering multi-chamber stimulation and pacing therapy. In addition, other subQ leads connecting with subQ electrodes can be used with the present invention (not shown). The subQ extra cardiac electrodes are preferably extra vascular and can be, e.g., paddle electrodes or coil electrodes mounted subcutaneously outside of the rib cage, but are not limited thereto. To sense atrial cardiac signals and to provide right atrial chamber stimulation therapy, the ICD 10 is coupled to the implantable right atrial lead 20 having at least an atrial tip electrode 22, which typically is implanted in the patient's right atrial appendage.

To sense left atrial and ventricular cardiac signals and to provide left-chamber pacing therapy, the ICD 10 is coupled to the "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that RV coil electrode 36 will be positioned in the right ventricle and the SVC coil electrode 38 will be positioned in the SVC. Accordingly, the right ventricular lead 30 is capable of receiving cardiac signals and delivering stimulation in the form of pacing and shock therapy to the right ventricle.

FIG. 2 shows a simplified block diagram of the ICD 10, which is capable of treating AF with stimulation of atrial vagal fat pads and AATP. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired vagal stimulation and pacing.

A housing 240 of the ICD 10, shown schematically in FIG. 2, is often referred to as the "can," "case" or "case electrode" and may be programmably selected to act as the return electrode for all "unipolar" modes. The housing 240 may further be used as a return electrode alone or in combination with one or more of the coil electrodes, 28, 36, and 38 for shocking purposes. The housing 240 further includes a connector (not shown) having a plurality of terminals, 242, 244, 246, 248, 252, 254, 256, 258, 264, 265, 266 and 267 (shown schematically and, for convenience, the names of the electrodes to which they are connected are shown next to many of the terminals). As such, to achieve right atrial sensing and pacing, the connector includes at least a right atrial tip terminal ($A_R$ TIP) 242 adapted for connection to the atrial tip electrode 22.

To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection via an exemplary coronary sinus lead 24, designed to receive left atrial and ventricular cardiac signals and to deliver left atrial and ventricular pacing therapy using at least a left ventricular tip electrode 26, left atrial pacing therapy using at least a left atrial ring electrode 27, and shocking therapy using at least a left atrial coil electrode 28.

To support right chamber sensing, pacing, and shocking the connector also includes a right ventricular tip terminal ($V_R$ TIP) 252, a right ventricular ring terminal ($V_R$ RING) 254, a right ventricular shocking terminal (RV COIL) 256, and an SVC shocking terminal (SVC COIL) 258, which are configured for connection to the right ventricular tip electrode 32, the right ventricular ring electrode 34, the RV coil electrode 36, and the SVC coil electrode 38, respectively.

The stimulation device 10 is also shown in electrical communication with the patient's heart 112 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 112 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

At the core of the ICD 10 is a programmable microcontroller 260, which controls the various modes of stimulation therapy. As is well known in the art, the microcontroller 260 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 to Mann et. al. which is expressly incorporated herein by reference in its entirety and the state-machines of U.S. Pat. Nos. 4,712,555 to Sholder which is expressly incorporated herein by reference in its entirety and 4,944,298 to Sholder which is expressly incorporated herein by reference in its entirety. For a more detailed description of the various timing intervals used within the ICD's and their inter-relationship, see U.S. Pat. No. 4,788,980 (Mann et. al.), which is expressly incorporated herein by reference in its entirety.

As shown in FIG. 2, an atrial pulse generator 270 and a ventricular pulse generator 272, generate pacing stimulation pulses for delivery by the right atrial lead 20, the right ventricular lead 30, and/or the coronary sinus lead 24 via an electrode configuration switch 274. More specifically, the atrial pulse generator 270 produces atrial pacing pulses (also known as A-pulses), and the ventricular pulse generator 272 produces ventricular pacing pulses (also known as V-pulses). In addition, a fat pad pulse generator 263 generates pulses to stimulate the atrial vagal fat pads. It is understood that in order to provide stimulation therapy in each of the four chambers of the heart, the atrial, ventricular and fat pad pulse generators 270, 272 and 263 may include dedicated, independent pulse generators, multiplexed pulse generators, or shared pulse generators. The pulse generators 270, 272 and 263 are controlled by the microcontroller 260 via appropriate control signals 276, 278 and 262, respectively, to trigger or inhibit the stimulation pulses.

The microcontroller 260 further includes timing control circuitry 279, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atria-ventricular (AV) delay, inter-ventricular (RV-LV) delay, atrial inter-conduction (A-A) delay, ventricular inter-conduction (V-V) delay, and pacing rate.

The switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art.

The atrial sensing circuits 282 and ventricular sensing circuits 284 may also be selectively coupled to the right atrial lead 20, the coronary sinus lead 24, and the right ventricular lead 30, through the switch 274 for detecting the presence of cardiac activity in each of the four chambers of the heart. Accordingly, the atrial (ATR. SENSE), ventricular (VTR. SENSE) and SVT (FAT PAD SENSE) sensing circuits 282, 284 and 285 may include dedicated sense amplifiers, multiplexed amplifiers, or shared amplifiers. The switch 274 determines the "sensing polarity" of the cardiac signal by selectively closing the appropriate switches, as is also known in the art. In this way, a clinician may program the sensing polarity independent of the stimulation polarity.

Each of the sensing circuits, 282, 284 and 285, preferably employs one or more low power, precision amplifiers with programmable gain and/or automatic gain control, band pass filtering, and a threshold detection circuit, as known in the art, to selectively sense the cardiac signal of interest. For example, the atrial sensing circuit 282 can sense P-waves, the ventricular sensing circuit 284 can sense R-waves and the fat pad sensing circuit 285 can sense hyperactivity in the fat pads. A P-wave occurs when that atrium contracts naturally, and is thus indicative of an intrinsic atrial contraction. Similarly, an R-wave occurs when the ventricle contracts naturally, and is thus indicative of an intrinsic ventricular contraction. The ICD monitors either continually for fat pad hyperactivity 261 or alternatively monitors at specified intervals. The atrial sensing circuits (FAT PAD SENSE) 285 can be selectively coupled through the switch 274 to the fat pad sensing electrodes 264 and 265 shown in FIG. 2. The atrial sensing circuit 285 in turn, receives control signals over signal lines, 268 from the fat pad monitor 261. Sensing circuit 285 can be connected to the output of microcontroller 260. The automatic gain control enables the ICD 10 to deal effectively with the difficult problem of sensing the low amplitude signal characteristics of AF or hyperactivity. As explained in U.S. Pat. No. 6,865,420, to Kroll, which is expressly incorporated herein by reference in its entirety, it is also possible that the ICD 10 includes further sensing circuitry (not shown) that is dedicated to sensing a cardiac signal that is evaluated for changes indicative of myocardial ischemia by an ischemia detector (not shown).

It is well known in the art to detect P-waves and R-waves using thresholding, where corresponding thresholds (e.g., a P-wave threshold and an R-wave threshold) can be either constant or dynamically adjustable. Examples of dynamically adjustable thresholds are provided, for example, in U.S. Pat. No. 4,768,511 to DeCote, and U.S. Pat. No. 5,891,048 to Nigam et al and in commonly assigned U.S. patent application Ser. No. 10/948,026 to Nabutovsky et al., filed Nov. 24, 2004, each of which is expressly incorporated by reference herein in their entirety. Using thresholding algorithms, and/or alternative types of algorithms, it also is well known how to detect the approximate locations of P-waves and R-waves.

In an embodiment of the present invention, the hyperactivity can be detected directly. In an alternative embodiment of the present invention, the hyperactivity can be detected indirectly. In various embodiments of the present invention, the threshold for detection for direct or indirect detection can be set to values between 5% and 20% above the baseline values. In various embodiments of the present invention, the baseline frequency can be established over a period of time. In an embodiment of the present invention, the baseline frequency can be determined for individual patients. The baseline rate can be determined before hand for individual patients and preprogrammed into the ICD. In an alternative embodiment of the present invention, the baseline and threshold values can be adjusted with time over extended monitoring to adjust for extrinsic influences. In another embodiment, the baseline rate can also be adjusted based on the preprogrammed value and individual patient data obtained through monitoring. In various embodiments of the invention, dampening of the signal can be used to circumvent electronic noise and/or sporadic fluctuations triggering false hyperactivity detection. In various embodiments of the invention, the dampening can be carried out by signal averaging over 'n' points, where 'n' is chosen based on the frequency of sampling such that a minimum of 3 sampling points or sampling for a minimum of 3 milliseconds are carried out where the average signal observed over this interval are recorded above the threshold. It is noted, that the term "based on" as used herein, means "based at least on part on", unless otherwise specified.

In order to directly detect hyperactivity, action potentials emanating from ganglianated plexi (GP) are analyzed over a time period. Hyperactivity can be detected when monitoring a fat pad, the frequency of action potentials increases above a predetermined threshold relative to a baseline. In various embodiments of the present invention, the threshold can be set to approximately 10% above the baseline frequency.

In an alternative embodiment of the present invention, the hyperactivity can be detected indirectly by monitoring the shape and characteristics of the action potentials detected at a fat pad. When experiencing hyperactivity at a fat pad, the width of the action potential becomes narrower while the downward curve contains a latent bulge. This change in the shape of an action potential can be said to exhibit "early after depolarization" (EAD). The reduction in the width of the action potential can be used as an indirect measure of hyperactivity. The width of the action potential can be determined by measuring the peak full width at half maximum peak height (FWHM). Upon monitoring of the peak FWHM, a reduction in the FWHM by more than a threshold value of greater than approximately 5% FWHM can be used to determine hyperactivity.

Alternatively, the EAD characteristic can be used to indirectly detect hyperactivity. EAD can be observed after the action potential has reached a maximum voltage amplitude and is reducing back to a minimum (baseline) voltage amplitude. Before the action potential returns to the baseline value a significant delay can be observed. During the initial stages of EAD, a plateau can be encountered at a value significantly higher than the baseline. Detection of this plateau above a predetermined voltage threshold relative to a baseline can be used to detect hyperactivity. Detection of a plateau value greater than 10% of the baseline that is sustained for the duration of the PWHM can be used to detect hyperactivity. In a variation on this detection scheme, rather than triggering on the plateau that is sustained for FWHM time period, hyperactivity can be determined based on the extended time taken for the action potential to fall to baseline from 25% of the peak height. Hyperactivity can be detected when the time taken for an action potential to fall from 25% peak height to baseline exceeds by approximately 20% the normal time taken for the action potential to return to the baseline.

The outputs of the atrial, ventricular and fat pad sensing circuits 282, 284 and 285 are connected to the microcontroller 260 which, in turn, are able to trigger or inhibit the atrial, ventricular and fat pad pulse generators, 270, 272 and 263, respectively, in a demand fashion in response to the absence or presence of cardiac activity, in the appropriate chambers of the heart. The atrial pulse generator 270 provides an A-pulse for delivery to the atrium at appropriate times, e.g., on demand as needed to maintain a programmed or sensor-indicated heart rate. The ventricular pulse generator 272 similarly provides a V-pulse for delivery to the ventricle at appropriate times, e.g., on demand as needed to maintain a programmed or sensor-indicated heart rate. The fat pad pulse generator 263 provides stimulation to atrial vagal fat pads. The sensing circuits 282, 284 and 285, in turn, receive control signals over signal lines 286, 288 and 268 from the microcontroller 260 for purposes of sensing cardiac events at appropriate times, and for controlling the gain, threshold, polarization charge removal circuitry (not shown), and timing of any blocking circuitry (not shown) coupled to the inputs of the sensing circuits 288, 286 and 268.

For arrhythmia detection, the ICD 10 utilizes the atrial and ventricular sensing circuits 282 and 284 to sense cardiac signals to determine whether a rhythm is physiologic or pathologic. The timing intervals between sensed events (e.g., P-waves, R-waves, and depolarization signals associated with fibrillation are then classified by microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardio version shocks or defibrillation shocks, collectively referred to as "tiered therapy").

The microcontroller 260 can also utilize an arrhythmia detector 275 and a morphology detector 277 to recognize and classify arrhythmias so that appropriate therapy can be delivered. The morphology detector 277 may also be used to detect signal morphologies that are useful for detecting or confirming ischemic events. The arrhythmia detector 275 and morphology detector 277 can be implemented within the microcontroller 260, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 290. The data acquisition system 290 is configured to acquire intra-cardiac electrogram signals, convert the raw analog data into a digital signal (e.g., consisting of samples), and store the digital signals for later processing and/or telemetric transmission to an external device 202. Data acquisition system 290 is coupled to the right atrial lead 20, the coronary sinus lead 24, and right ventricular lead 30 through switch 274 to sample cardiac signals across any pair of desired electrodes.

Figure 1B:
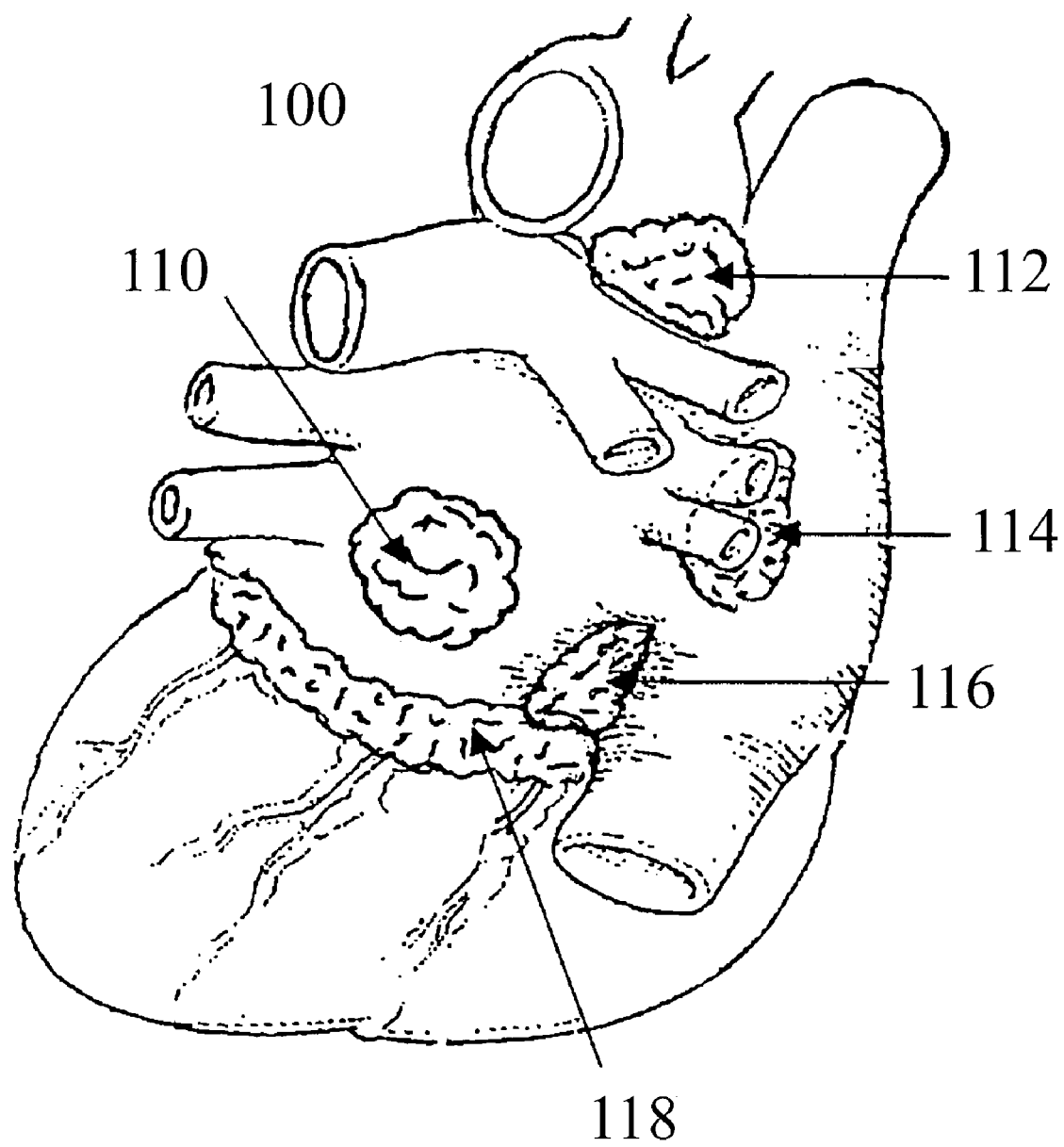
FIG. 1B shows five vagal fiber fat pad regions on or near the heart.

Parasympathetic nerve stimulation can be accomplished, e.g., either directly by electrode placement on/or around the vagus nerve (i.e., by placing the electrode in contact with GP or indirectly via electrode placement in the vicinity of the GP). For example, FIG. 1B shows the five sites 110, 112, 114, 116 and 118 for parasympathetic nerve stimulation electrodes capable of delivering inhibitory, stimulatory or excitatory bursts to a patient's parasympathetic nerve. Such electrodes can be optimally positioned, e.g., in the epicardial fat pad near the left atrium 110 fat pad, superior vena cava and aortic root (SVC-Ao) fat pad 112, right pulmonary vein-atrial (RPV) fat pad 114, inferior vena cava-left atrial (IVC-ILA) fat pad 116 or the coronary sinus (CS) fat pad 118. Other possible locations for the stimulation electrodes are in proximity to the cervical vagus where they are also capable of delivering stimulation bursts to the patient's vagus nerve. Additional and/or alternative locations for the parasympathetic stimulation electrodes are within the scope of the present invention, some of which are discussed below.

In an embodiment of the present invention, electrodes can remodel the shape of the ganglionated plexi (GP) fibers with a minimum of nerve damage. In an embodiment of the present invention, electrodes can remodel the shape of the fiber with no nerve damage. Frequent occurrences of AF result in adverse modeling. In an embodiment of the invention, by preventing AF a device is able to remodel the heart back to a healthy state.

In various embodiments of the present invention, pacing parameters include pacing locations, number of pacing electrodes, number of pacing stimuli, duration of pacing, stimulus amplitude, waveform shape, waveform pulse width, waveform polarity, frequency of pacing stimuli, synchronous pacing of multiple electrodes and simultaneous pacing of multiple electrodes. In various embodiment of the present invention, pacing parameters can be altered to optimize the outcome of the pacing.

In certain embodiments, constant current pacing at or near atrial vagal fat pads between approximately 10 mA and approximately 20 mA can be used to either prevent or terminate AF. In various embodiments, a sinusoidal voltage waveform can be administered to either prevent or terminate AF. In accordance with specific embodiments, biphasic stimulation of the one or more atrial vagal fat pad can be used to either prevent or terminate AF. In accordance with specific embodiments, in order to prevent or terminate AF, a pulse width of between approximately 20 microseconds and approximately 50 microseconds can be employed.

In accordance with specific embodiments, in order to terminate AF, one or more atrial vagal fat pad can be stimulated continuously for between approximately 10 sec and approximately 20 sec in combination with administration of AATP (described elsewhere). In various embodiments, the frequency of the pulsed waveform can be between approximately 5 Hz and approximately 30 Hz. In various embodiments, the frequency of the pulsed waveform can be increased from a low initial frequency incrementally.

In accordance with specific embodiments, in order to prevent AF, inhibitory stimulation can be administered at or near one or more atrial vagal fat pad for between approximately 1 min and approximately 90 min. In various embodiments, the frequency of the pulsed waveform can be between approximately 1 kHz and approximately 20 kHz. In various embodiments, the frequency of the pulsed waveform can be increased from a low initial frequency incrementally.

In accordance with specific embodiments, in order to prevent AF, excitatory stimulation can be administered at or near one or more atrial vagal fat pad for between approximately 1 min and approximately 90 min. In various embodiments, the frequency of the pulsed waveform can be high frequency. In alternative embodiments of the present invention the frequency of the pulsed waveform can be low frequency. The high frequency pulses can be between approximately 60 Hz and approximately 200 Hz. The low frequency pulses can be between approximately 1 Hz and approximately 5 Hz. In various embodiments, the frequency of the pulsed waveform can be increased from a low initial frequency incrementally between the high frequency range. In various embodiments, the frequency of the pulsed waveform can be increased from a low initial frequency incrementally between the low frequency range.

In accordance with specific embodiments, in order to prevent AF, one or more atrial vagal fat pad can be stimulated continuously for between approximately 10 sec and approximately 20 sec in combination with administration of AATP (described elsewhere). In various embodiments, the frequency of the pulsed waveform is between approximately 5 Hz and approximately 30 Hz. In various embodiments, the frequency of the pulsed waveform is increased from a low initial frequency incrementally.

The ICD 10 further includes a physiologic sensor 208 that can be used to detect changes in cardiac performance or changes in the physiological condition of the heart. Accordingly, the microcontroller 60 can respond by adjusting the various pacing parameters (such as rate, AV Delay, RV-LV Delay, V-V Delay, etc.). The microcontroller 260 controls adjustments of pacing parameters by, for example, controlling the stimulation pulses generated by the atrial and ventricular pulse generators 270 and 272. While shown as being included within the ICD 10, it is to be understood that the physiologic sensor 208 may also be external to the ICD 10, yet still be implanted within or carried by the patient. More specifically, the sensor 208 can be located inside the ICD 10, on the surface of ICD 10, in a header of ICD 10, or on a lead (which can be placed inside or outside the bloodstream).

Also shown in FIG. 2 is an activity sensor 217. The activity sensor 217 (e.g., an accelerometer) can be used to determine the activity of the patient. Such information can be used for rate responsive pacing, or to determine whether the patient is sufficiently at rest such that certain baseline measurements can be obtained. If the sensor 217 is a multi-dimensional accelerometer, then posture information can also be extracted. The following patents, which are expressly incorporated herein by reference in their entirety, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position". Simple activity sensors employ a piezoelectric crystal or a cantilever beam having a film of a piezoelectric polymer adhered to a surface of the beam. These are just a few exemplary types of activity sensors 217, which are not meant to be limiting.

The ICD 10 may also include a magnet detection circuitry (not shown), coupled to the microcontroller 260. It is the purpose of the magnet detection circuitry to detect when a magnet is placed over the ICD 10. A clinician may use the magnet to perform various test functions of the ICD 10 and/or to signal the microcontroller 260 that the external programmer 202 is in place to receive or transmit data to the microcontroller 260 through the telemetry circuit 201.

As further shown in FIG. 2, the ICD 10 can have an impedance measuring circuit 213, which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 260 further controls a shocking circuit 216 by way of a control signal 218. The shocking circuit 216 generates shocking pulses of low (up to about 0.5 Joules), moderate (about 0.5-10 Joules), or high energy (about 11 to 40 Joules), as controlled by the microcontroller 260. Such shocking pulses are applied to the patient's heart 12 through at least two shocking electrodes (e.g., selected from the left atrial coil electrode 28, the RV coil electrode 36, and the SVC coil electrode 38). As noted above, the housing 240 may act as an active electrode in combination with the RV electrode 36, or as part of a split electrical vector using the SVC coil electrode 38 or the left atrial coil electrode 28 (i.e., using the RV electrode as a common electrode).

Cardio-version shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, the microcontroller 260 is capable of controlling the synchronous or asynchronous delivery of the shocking pulses.

An approach for treating AF involves identification and ablation of parasympathetic (vagal) pathways to the atria, thus imparting selective parasympathetic denervation without disruption of sympathetic control. Since the mid 1980s, research has led to the identification of various "fat pads", which contain autonomic ganglia that innervate the atria and control atria-ventricular and sino-atrial nodal function. In patients suffering from atrial fibrillation, these ganglia are over-active relative to control patients. In an embodiment of the present invention, electrodes are placed at or near fat pads as a means of stimulating autonomic ganglia plexi (GP). In an embodiment of the invention, locating electrodes at fat pads in contact with nerve fibers measuring 30 to more than 200 micrometer in diameter within the adipose tissue coursing with atrial myocytes can be considered in contact with GP. In an embodiment of the invention, locating electrodes at fat pads associated with nerve fibers where scattered ganglia containing up to 20 cell bodies per section can be considered fat pads near GP. Embodiments of the present invention are not directed to the specific techniques that are used to detect the presence of fat pad hyperactivity after AF has been detected. Rather, certain embodiments of the present invention, as can be appreciated from the discussion above, can be thought of as based on the identification of fat pad hyperactivity and its use in an algorithm for the prevention of AF.

Parasympathetic nerve stimulation can be accomplished, e.g., either directly by electrode placement on/around the vagus nerve or indirectly via electrode placement in the vicinity of the vagus nerve. For example, FIG. 1B shows the five sites 110, 112, 114, 116 and 118 for parasympathetic nerve stimulation electrodes capable of delivering inhibitory, stimulatory or excitatory bursts to a patient's parasympathetic nerve. Such electrodes can be optimally positioned, e.g., in the epicardial fat pad near the left atrium 110 fat pad, superior vena cava and aortic root (SVC-Ao) fat pad 112, right pulmonary vein-atrial (RPV) fat pad 114, inferior vena cava-left atrial (IVC-ILA) fat pad 116 or the coronary sinus (CS) fat pad 118. Other possible locations for the stimulation electrodes are in proximity to the cervical vagus where they are also capable of delivering stimulation bursts to the patient's vagus nerve. Additional and/or alternative locations for the parasympathetic stimulation electrodes are within the scope of the present invention, some of which are discussed below.

The circuitry for stimulating a parasympathetic nerve can be in the same housing as the stimulation device 10, or in a separate housing (not shown). When the parasympathetic nerve stimulation circuitry is in a separate housing, connections between a parasympathetic nerve stimulation device and the stimulation device 10 can be hard-wired, or the two devices can communicate wirelessly.

The particular locations of the implanted components shown in FIG. 1A and FIG. 1B are merely illustrative and may not necessarily correspond to actual implant locations. In general, any of the components can be implanted in any location that is effective for its intended purposes with, preferably, all components being implanted extracardially and extravascularly.

In accordance with embodiments of the present invention, one or more pairs of the subQ electrodes (not shown) are used to detect and treat arrhythmias.

Advantageously, a data acquisition system 290 can be coupled to the microcontroller 260, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 to Decote, Jr. which is expressly incorporated herein by reference in its entirety; U.S. Pat. No. 4,708,142 to Decote, Jr. which is expressly incorporated herein by reference in its entirety; U.S. Pat. No. 4,686,988 to Sholder which is expressly incorporated herein by reference in its entirety; U.S. Pat. No. 4,969,467 to Callaghan et. al. which is expressly incorporated herein by reference in its entirety; and U.S. Pat. No. 5,350,410 to Mann et. al. which is expressly incorporated herein by reference in its entirety. The type of capture detection system used is not critical to the present invention.

The microcontroller 260 is further coupled to a memory 294 by a suitable data/address bus 296, wherein the programmable operating parameters used by the microcontroller 260 are stored and modified, as required, in order to customize the operation of the pacing device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, the operating parameters of the implantable device 10 can be non-invasively programmed into the memory 294 through a telemetry circuit 201 in telemetric communication with the external device 202, such as a programmer, trans telephonic transceiver, or a diagnostic system analyzer. The telemetry circuit 201 can be activated by the microcontroller 260 by a control signal 206. The telemetry circuit 201 advantageously allows intra cardiac electrograms and status information relating to the operation of the device 10 (as contained in the microcontroller 260 or memory 294) to be sent to an external device 202 through an established communication link 205.

For examples of such devices, see U.S. Pat. No. 4,809,697, to Causey, III et al. entitled "Interactive Programming and Diagnostic System for use with Implantable Pacemaker" which is expressly incorporated herein by reference in its entirety; U.S. Pat. No. 4,944,299, to Silvian entitled "High Speed Digital Telemetry System for Implantable Device" which is expressly incorporated herein by reference in its entirety; and U.S. patent application Ser. No. 09/223,422, to McClure et al. filed Dec. 30, 1998, entitled "Efficient Generation of Sensing Signals in an Implantable Medical Device such as a Pacemaker or ICD" which is expressly incorporated herein by reference in its entirety.

The pacing device 10 additionally includes a battery 211, which provides operating power to all of the circuits shown in FIG. 2. If the pacing device 10 also employs shocking therapy, the battery 211 can be capable of operating at low current drains for long periods of time, and then be capable of providing high-current pulses (for capacitor charging) when the patient requires a shock pulse. The battery 211 can also have a predictable discharge characteristic so that elective replacement time can be detected.

Now that an exemplary implantable stimulation device has been described, specific embodiments of the present invention will be now be described with reference to the high level flow diagrams of FIGS. 3A, 3B, 3C and 3D. In FIGS. 3A, 3B, 3C and 3D, flow diagrams are shown describing an overview of the operation and novel features implemented in various embodiments of the device 10. In the flow diagrams described herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of the stimulation device. Those skilled in the art may readily write such a control program based on the flow diagrams and other descriptions presented herein.

Detecting AF/Hyperactivity and Terminating with AATP and Fat Pad Stimulation

Figure 3A:
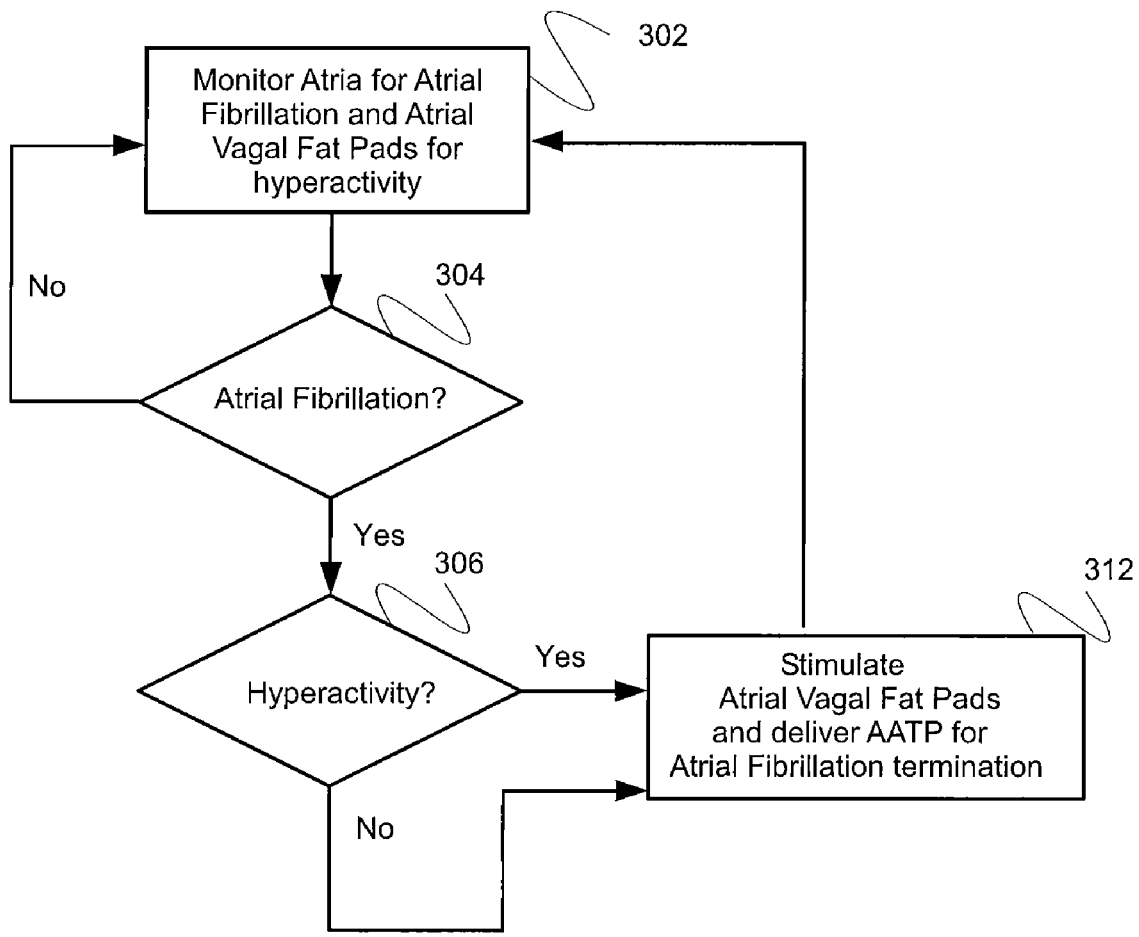
FIG. 3A is a high level flow diagram useful for describing AF termination embodiments of the present invention involving atrial vagal fat pad stimulation and AATP.

In FIG. 3A, a flow diagram is shown describing an overview of the operation and novel features implemented in one embodiment of the device 10.

When AF and hyperactivity at or near one or more atrial vagal fat pad have been detected, the AF can be terminated by administering AATP together with stimulation of one or more atrial vagal fat pad. Referring first to FIG. 3A, at a step 302 an electrogram (EGM) is monitored for the purpose of detecting AF. Independently, one or more atrial vagal fat pads are monitored for hyperactivity. Since it is well known how to detect AF, there is no need to describe this aspect of step 302 in significant additional detail. Exemplary electrodes for sensing AF and hyperactivity were discussed above with reference to FIG. 1 and FIG. 2. Briefly, the right atrial tip terminal ($A_R$ TIP) 242 shown in FIG. 2 connected to electrode 22 shown in FIG. 1A, can be used for right atrial sensing. In various embodiments of the present invention, single or multiple electrodes (up to 10 in unipolar and/or bipolar formats) can be placed in one or more vagal fibers selected from the group consisting of the epicardial fat pad near the superior vena cava and aortic root (SVC-Ao), left atrium fat pad, right pulmonary vein (RPV) atrial fat pad and inferior vena cava-inferior left atrial (IVC-ILA) fat pad. One or more electrodes 264 and 265 (see FIG. 2) placed at one or more fat pad positions 110, 112, 114, 116 and 118 (see FIG. 1B) can be used for sensing hyperactivity. Exemplary algorithms for determining whether fat pad hyperactivity is present are discussed above. However, it is noted that alternative fat pad hyperactivity algorithms can be used, while still being within the spirit and scope of the present invention.

At a step 304, the atrial activity can be analyzed to determine if AF is occurring. The atrial sensing circuits (ATR. SENSE) 282 can be selectively coupled to the right atrial lead 20. The right atrial lead 20 can be connected with electrode 22 shown in FIG. 1A. The atrial sensing circuit connects through the switch 274 to the right atrial tip terminal ($A_R$ TIP) 242 shown in FIG. 2. The atrial sensing circuit 282 in turn, receives control signals over signal lines, 286 from the AF detector 281. An EGM can be used to monitor the heart and the atrial activation pulses produced therein. Depending on the stage of AF, whether it is chronic or advanced and more regular, AF can be readily detected from the EGM. At the chronic stage, AF can be detected by monitoring RR intervals (i.e., the intervals between sensed 'R' waves). Methods for analyzing EGM's to determine variations in the RR intervals are well known in the art. This is just one example of a method to detect AF known to one of ordinary skill in the art. Any technique for detecting AF can be alternatively used. When intermittent, AF can be detected as an alteration in the complexity of RR interval dynamics or changes in the conduction velocity through the AV node, P wave shape or P wave frequency representations. AF is generally occurring when the atrial rate is in the region of 450/min to 600/min, the ventricular response rate is 130/min and the atrial rate is irregular.

At step 306, the neural activity at one or more fat pad being monitored can be analyzed for hyperactivity. The atrial sensing circuits (FAT PAD SENSE) 285 can be selectively coupled through the switch 274 to one or more of the fat pad sensing electrodes 264 and 265 shown in FIG. 2. The atrial sensing circuit 285 in turn, receives control signals over signal lines 268 from the fat pad monitor 261. The output of the sensing circuit 285 can be provided to the microcontroller 260. The microcontroller 260 can in turn trigger the AATP and the fat pad inhibitory stimulation. Neural activity in the fat pads is categorized as 'hyperactivity' when the rate of the neural activity exceeds a given rate. The given rate can be determined before hand for individual patients and preprogrammed into the ICD. The given rate can also be adjusted based on the preprogrammed value and individual patient data.

Then AATP and atrial vagal fat pad stimulation can be initiated at step 312, using the results of the monitoring for hyperactivity, as will be described below. The right atrial tip terminal ($A_R$ TIP) 242 shown in FIG. 2 connected to electrode 22 shown in FIG. 1A, can be used for right atrial pacing. Methods for delivering AATP are well known in the art. Stimulatory fat pad electrodes 266 and 267 (see FIG. 2) placed at one or more fat pad positions 110, 112, 114, 116 and 118 (see FIG. 1B) can be used for providing inhibitory stimulation at the fat pad position(s).

In accordance with specific embodiments, in order to terminate AF, one or more atrial vagal fat pad can be stimulated continuously for between approximately 10 sec and approximately 20 sec in combination with administration of AATP (described elsewhere). In accordance with specific embodiments, biphasic stimulation of the one or more atrial vagal fat pad can be used to terminate AF. In certain embodiments, constant current pacing at between approximately 10 mA and approximately 20 mA can be used to terminate AF. In various embodiments, a sinusoidal voltage waveform can be administered to terminate AF. In various embodiments, the frequency of the pulsed waveform can be between approximately 5 Hz and approximately 30 Hz. In various embodiments, the frequency of the pulsed waveform can be increased from a low initial frequency incrementally. In accordance with specific embodiments, in order to terminate AF or atrial vagal fat pad activation, a pulse width of between approximately 20 microseconds and approximately 50 microseconds can be employed.

During AF, hyperactivity at the fat pads is highly associated with the onset and maintenance of AF. Thus, by monitoring the neural activity from the fat pads, the timing of AATP delivery to terminate AF can be optimized. In an embodiment of the present invention, when hyperactivity at the fat pad is detected, AATP from a single site or multiple sites can immediately be delivered to terminate AF if AF was detected. In an embodiment of the present invention, vagal fibers innervating the atrial fat pads can be stimulated to modulate the vagal tone in the atria resulting in pre-conditioning of the atria to optimize the pacing modes and timing of AATP for AF termination. In an embodiment of the present invention, such a pacing scheme together with fat pad stimulation can be more effective in preventing the recurrence of AF. In an embodiment of the present invention, AATP can be triggered by the vagal stimulation. That is there can be a fixed delay between the initial atrial vagal fat pad stimulation and the trigger for administration of AATP.

In an alternative embodiment of the present invention, AATP can be carried out sequential with vagal stimulation. That is the administration of AATP can be the trigger for the initial atrial vagal fat pad stimulation. In another embodiment of the present invention, AATP can be carried out simultaneous with vagal stimulation. That is the administration of atrial vagal fat pad stimulation and the administration of AATP can both be triggered by the same event such that at least the initial pacing or fat pad stimulation occur simultaneously. In another alternative embodiment of the present invention, AATP can be carried out synchronous with the vagal stimulation. That is there can be a delay between the administration of AATP and the trigger for the initial atrial vagal fat pad stimulation.

In an embodiment of the present invention, the atrial vagal fat pad stimulated, can be selected based on results of monitoring of the one or more atrial vagal fat pad for hyperactivity and/or a recorded site of hyperactivity. In an embodiment of the invention, when the neural activity of at least two atrial vagal fat pads are monitored, then the atrial electrode selected for AATP can be closest to the atrial vagal fat pad having a longest duration of hyperactivity. In an alternative embodiment of the invention, the atrial electrode selected for AATP can be closest to the atrial vagal fat pad having a most intense action potential of hyperactivity. In another embodiment of the invention, the atrial electrode selected for AATP can be closest to the atrial vagal fat pad having a most irregular hyperactivity.

In an embodiment of the present invention, if no hyperactivity is observed then the atrial vagal fat pad stimulated can be a default site. The default site can be programmed based on previous occurrences of AF with the patient that were successfully addressed.

In an embodiment of the present invention, if inhibitory stimulation is applied to only one fat pad, then the atrial electrode selected for AATP can be the closest to the stimulated atrial vagal fat pad. In an alternative embodiment of the invention, if inhibitory stimulation is applied to only one fat pad and the inhibitory stimulation and pacing did not terminate the AF, then another atrial electrode can be selected for AATP, the electrode can be the next closest to the stimulated atrial vagal fat pad. The next closest site is defined after excluding the furthest site from consideration as the site furthest to the stimulated fat pad.

In an embodiment of the present invention, one or more intrapericardial electrodes can be implanted through the subxiphoid approach to monitor for AF and/or hyperactivity. The subxiphoid pericardial approach of exposing the epicardial surface of the heart has previously been used when percutaneous epicardial access fails or where pericardial adhesions from prior cardiac surgery are present.

In an embodiment of the present invention, inhibitory stimulation of the one or more atrial vagal fat pad coincides approximately in time with delivering AATP. In an alternative embodiment of the present invention, inhibitory stimulation of the one or more atrial vagal fat pad precedes in time delivering AATP. Further in this embodiment of the invention, the site selected for AATP can be based on the AATP site most affected by the preceding atrial vagal fat pad stimulation. In another embodiment of the present invention, inhibitory stimulation of the one or more atrial vagal fat pad can be approximately synchronous in time with delivering AATP. In another alternative embodiment of the present invention, inhibitory stimulation of the one or more atrial vagal fat pads can trigger delivering AATP.

In an embodiment of the present invention, inhibitory stimulation can be administered at two or more atrial vagal fat pads approximately simultaneously in time. In an alternative embodiment of the present invention, inhibitory stimulation can be administered at two or more atrial vagal fat pads sequentially.

Predicting AF and Preventing Through Inhibitory Fat Pad Stimulation

Figure 3B:
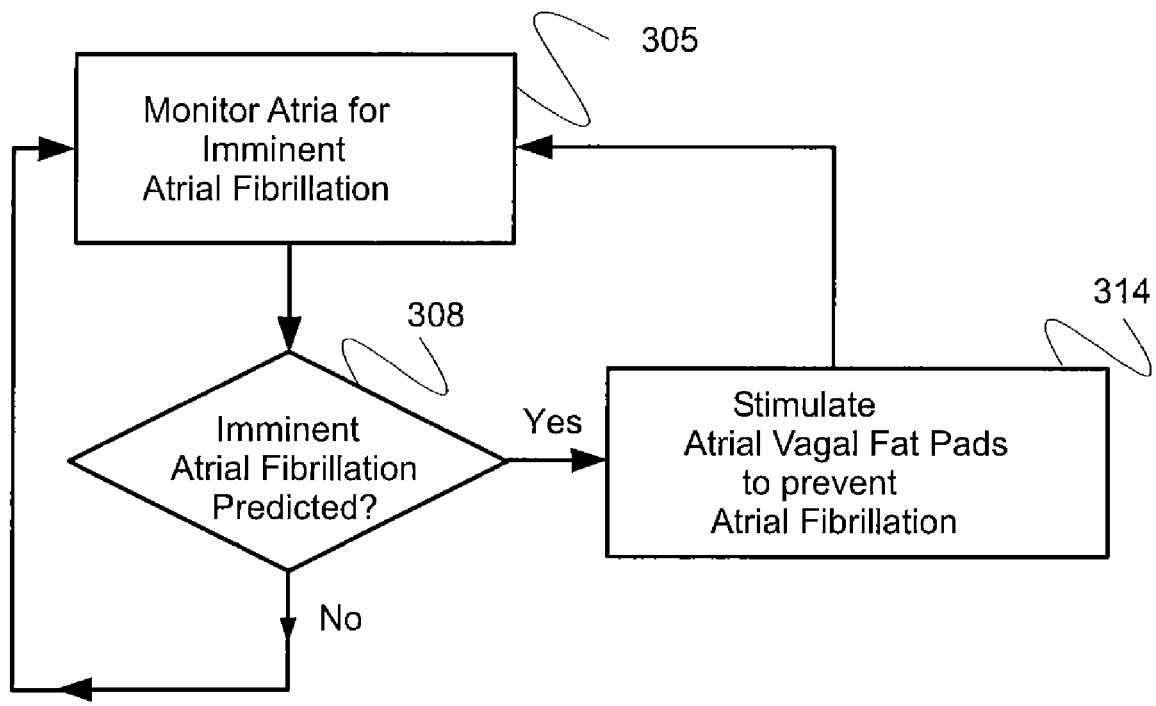
FIG. 3B is a high level flow diagram useful for describing AF prevention embodiments of the present invention.

When AF is predicted, then the AF can be prevented by administering inhibitory stimulation at or near one or more atrial vagal fat pad. Referring to FIG. 3B, at a step 305, atrial activity can be analyzed to determine if AF is imminent. This can involve monitoring the atria for PACs and/or monitoring the atrial vagal fat pads for hyperactivity. If either PACs or hyperactivity are occurring then inhibitory stimulation can be administered to one or more atrial vagal fat pads.

At a step 308, the atrial activity can be analyzed to determine if AF is predicted to occur. In an embodiment of the present invention, AF can be predicted based on detecting PACs irrespective of changes in the HR. In an embodiment of the invention, PACs are counted over a span of time. In an embodiment of the invention, when the number of PACs changes with time by more than a predetermined ratio or percentage then AF can be predicted. In an embodiment of the invention, the predetermined ratio or percentage can be 10%. In an embodiment of the present invention, based on detecting PACs an inhibitory stimulation of the fat pads can be administered to prevent AF. In an alternative embodiment of the present invention, based on detecting hyperactivity an inhibitory stimulation of the fat pads can be administered to prevent AF.

At step 314, atrial vagal fat pads can be stimulated to prevent AF from occurring. For example, stimulatory fat pad electrodes 266 and/or 267 (see FIG. 2) placed at fat pad positions 110, 112, 114, 116 and/or 118 (see FIG. 1B) can be used for providing inhibitory stimulation at the fat pad positions.

In accordance with specific embodiments, in order to prevent AF, inhibitory stimulation can be administered at or near one or more atrial vagal fat pad for between approximately 1 min and approximately 90 min. In accordance with specific embodiments, biphasic stimulation of the one or more atrial vagal fat pad can be used to prevent AF or prevent atrial vagal fat pad activation leading to AF. In certain embodiments, constant current pacing at between approximately 10 mA and approximately 20 mA can be used to prevent AF. In various embodiments, a sinusoidal voltage waveform can be administered to prevent AF. In various embodiments, the frequency of the pulsed waveform can be between approximately 1 kHz and approximately 20 kHz. In various embodiments, the frequency of the pulsed waveform can be increased from a low initial frequency incrementally. In accordance with specific embodiments of the present invention, in order to prevent AF, a pulse width of between approximately 2 millisecond and approximately 10 millisecond can be employed.

Predicting AF and Preventing Through Excitatory Fat Pad Stimulation

Figure 3C:
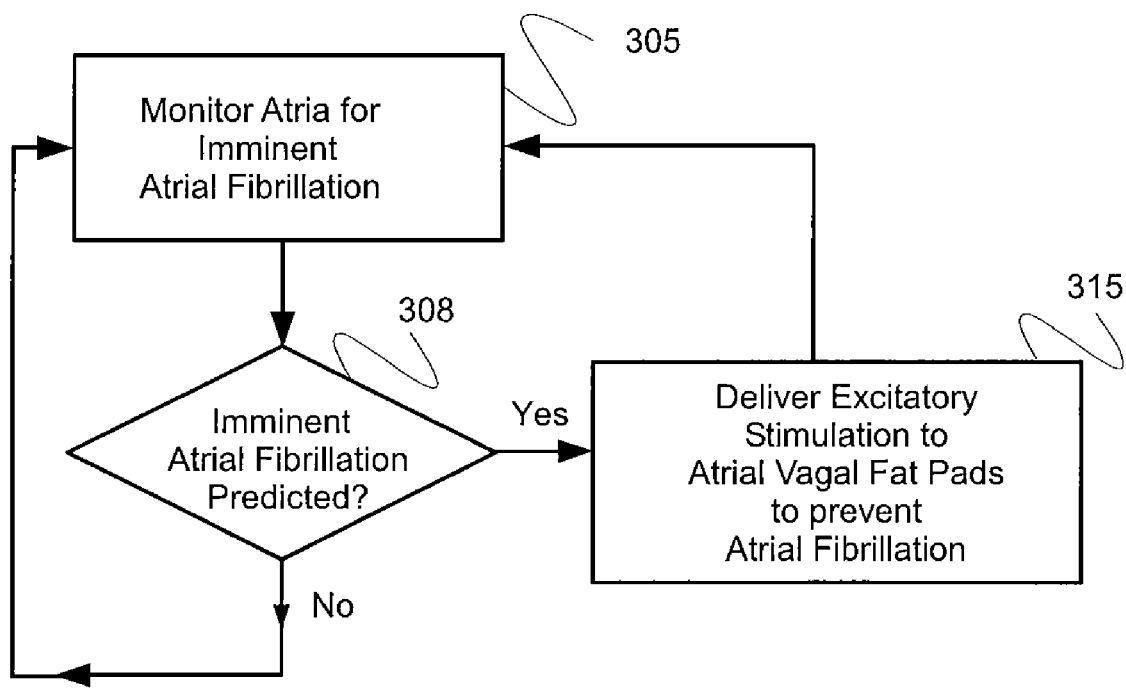
FIG. 3C is a high level flow diagram useful for describing AF prevention embodiments of the present invention involving excitatory stimulation.

When AF is predicted, then the AF can be prevented by administering excitatory stimulation at or near one or more atrial vagal fat pad. In an embodiment of the present invention, AF is predicted by either the detection of PACs or by the detection of hyperactivity. Referring to FIG. 3C, at a step 305, the activity in the atria can be analyzed to determine if AF is imminent. This involves monitoring the atria for PACs and monitoring the atrial vagal fat pads for hyperactivity. If either PACs or hyperactivity is occurring then excitatory stimulation can be administered to one or more atrial vagal fat pads. Since in FIG. 3C, step 305 is virtually identical to step 305 described above with reference to FIG. 3B, it need not be described again in the same detail.

Since step 308 is virtually identical to step 308 described above with reference to FIG. 3B, it need not be described again in detail.

At step 315, an excitatory stimulation can be administered to the atrial vagal fat pads to deplete the neurons innervating the fat pads of neurotransmitters and thereby prevent AF. Acetylcholine, one of the neurotransmitter released by the vagal nerve ending at the heart reduces the action potential duration and shortens the refractory period of the atrial muscle. As a result, additional R waves or re-entrant wavelets can be formed causing AF. By stimulating the release of neurotransmitters over a period of time the store of neurotransmitters at the nerve ending can be depleted and therefore the effect of neurotransmitter release can be minimized.

In an embodiment of the present invention, prolonged stimulation at either high or low frequency at the sub-cardio-threshold level, can be used without depolarizing the atrial tissue. In an embodiment of the present invention, prolonged stimulation at either high or low frequency at the sub-cardio-threshold level, can cause the release of the neurotransmitters. In an embodiment of the present invention, prolonged stimulation at either high or low frequency at the sub-cardio-threshold level, can deplete the stores of neurotransmitters at the nerve endings. In an embodiment of the present invention, prolonged stimulation at either high or low frequency at the sub-cardio-threshold level can minimize the effect of further neurotransmitter release and thereby demolish the effect of hyperactivity mediated through fat pad neurotransmitter release.

In accordance with specific embodiments, in order to prevent AF, excitatory stimulation can be administered at or near one or more atrial vagal fat pad for between approximately 1 min and approximately 90 min. In accordance with specific embodiments, biphasic stimulation of the one or more atrial vagal fat pad can be used to prevent AF or prevent atrial vagal fat pad activation leading to AF. In certain embodiments, constant current pacing at between approximately 10 mA and approximately 20 mA can be used to prevent AF. In various embodiments, a sinusoidal voltage waveform can be administered to prevent AF. In an embodiment of the present invention, the frequency of the pulsed waveform can be high frequency. The high frequency pulses can be between approximately 60 Hz and approximately 200 Hz. In alternative embodiment of the present invention the frequency of the pulsed waveform can be low frequency. The low frequency pulses can be between approximately 1 Hz and approximately 5 Hz. In various embodiments, the frequency of the pulsed waveform can be increased from a low initial frequency incrementally between the high frequency range. In various embodiments, the frequency of the pulsed waveform can be increased from a low initial frequency incrementally between the low frequency range. In accordance with specific embodiments of the present invention, in order to prevent AF, a pulse width of between approximately 2 millisecond and approximately 10 millisecond can be employed.

Detecting Hyperactivity and Preventing AF with AATP and Inhibitory Stimulation

Figure 3D:
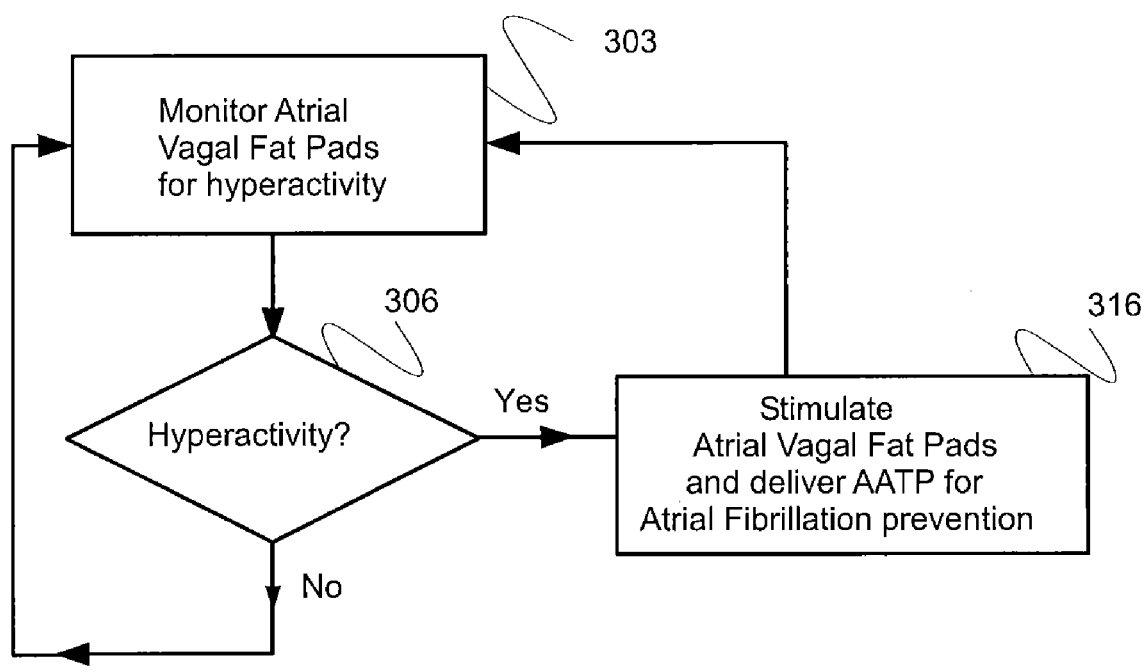
FIG. 3D is a high level flow diagram useful for describing AF prevention embodiments of the present invention involving atrial vagal fat pad stimulation and AATP.

When hyperactivity at or near one or more atrial vagal fat pad have been detected, administering AATP together with stimulation of one or more atrial vagal fat pads can be undertaken to prevent AF. Referring to FIG. 3D, at a step 303 one or more atrial vagal fat pad electrodes for detecting hyperactivity can be monitored using an implantable device (e.g., a monitor, pacemaker or ICD). Exemplary electrodes for sensing hyperactivity were discussed above with reference to FIG. 1 and FIG. 2.

At step 306, the neural activity at one or more fat pads being monitored can be analyzed for hyperactivity. Since step 306 is virtually identical to step 306 described above with reference to FIG. 3A, it need not be described again in detail.

Provided hyperactivity can be detected then AATP and atrial vagal fat pad stimulation can be initiated at 316. Since step 316 is virtually identical to step 312 described above with reference to FIG. 3A, it need not be described again in detail.

In accordance with specific embodiments, in order to prevent AF, one or more atrial vagal fat pad can be stimulated continuously for between approximately 10 sec and approximately 20 sec in combination with administration of AATP (described elsewhere). In accordance with specific embodiments, biphasic stimulation of the one or more atrial vagal fat pad is used to prevent AF or prevent atrial vagal fat pad activation leading to AF. In certain embodiments, constant current pacing at between approximately 10 mA and approximately 20 mA can be used to prevent AF. In various embodiments, a sinusoidal voltage waveform is administered to prevent AF. In various embodiments, the frequency of the pulsed waveform is between approximately 5 Hz and approximately 30 Hz. In various embodiments, the frequency of the pulsed waveform is increased from a low initial frequency incrementally. In accordance with specific embodiments, in order to prevent AF, a pulse width of between approximately 20 microseconds and approximately 50 microseconds can be employed.

Since embodiments of the present invention are intended to be used with a chronically implanted device, each time the device assesses AF and or atrial vagal fat pads neural activity, the device can store information indicative of the patients status so that it can be compared with one or more previous assessments and/or one or more future assessments, thereby enabling the device to track changes in the patient's AF or neural activity at or near atrial vagal fat pads. In other words, steps 302-312, 305-314, 305-315 and 303-316 can be monitored at different time intervals (e.g., when not pacing, continually, multiple times per day, etc.) so that changes in a patient's AF and neural activity can be monitored.

In an embodiment, a patient is alerted when a level of PACs or hyperactivity is sufficiently high to warrant an alert, thereby allowing the patient to respond appropriately. In an embodiment, a therapy can be triggered in response to assessing PACs or hyperactivity. One type of therapy would be for an implanted device (e.g., device 10) to initiate AATP and/or stimulate the vagal fat pad as described. Alternatively or in addition to stimulating the vagal fat pad an alert could be a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, AF may be avoided, or if it does occur, the patient will be less dangerous to themselves and others if the patient is resting when the AF occurs (as opposed, e.g., to driving a car).

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable device, a method for preventing atrial fibrillation (AF), the method comprising:
    (a) monitoring for imminent AF; and
    (b) in response to predicting imminent AF, delivering sub excitatory stimulation to one or more atrial vagal fat pad to thereby prevent AF.

2. The method of claim 1, wherein step (a) includes:
    (a.1) monitoring for premature atrial contractions; and
    (a.2) predicting whether AF is imminent based on premature atrial contractions detected during said monitoring at step (a.1).

3. The method of claim 1, wherein step (a) includes:
    (a.1) monitoring at least one atrial vagal fat pad for hyperactivity; and
    (a.2) predicting whether AF is imminent based on atrial vagal fat pad hyperactivity detected during said monitoring at step (a.1).

4. The method of claim 1, wherein one or more intrapericardial electrodes implanted through the subxiphoid approach are used to monitor for imminent AF.

5. The method of claim 1, wherein the sub excitatory stimulation is between approximately 85% and approximately 95% of the minimum amount of stimulation that is required for excitatory stimulation, where excitatory stimulation causes neurotransmitter release from neurons innervating the one or more atrial vagal fat pad, and where sub excitatory stimulation does not cause release of neurotransmitters from neurons innervating the one or more atrial vagal fat pad but does cause a change in properties of neurons innervating the one or more atrial vagal fat pad.

6. The method of claim 1, wherein step (b) also includes delivering atrial anti-tachycardia pacing (AATP), in response to predicting imminent AF.

7. In an implantable device for preventing atrial fibrillation (AF), comprising:
    a pulse generator;
    a lead including at least one electrode that is coupleable to the pulse generator; and
    a controller configured to monitor for imminent AF, and in response to predicting imminent AF, to cause the pulse generator to deliver sub excitatory stimulation via the lead to one or more atrial vagal fat pad, to thereby prevent AF.

8. The implantable device of claim 7, wherein the controller is configured to monitor for premature atrial contractions, and to predict whether AF is imminent based on detected premature atrial contractions.

9. The implantable device of claim 7, wherein the controller is configured to monitor at least one atrial vagal fat pad for hyperactivity, and to predict whether AF is imminent based on detected atrial vagal fat pad hyperactivity.

10. The implantable device of claim 8, wherein the sub excitatory stimulation is between approximately 85% and approximately 95% of the minimum amount of stimulation that is required for excitatory stimulation, where excitatory stimulation causes neurotransmitter release from neurons innervating the one or more atrial vagal fat pad, and where sub excitatory stimulation does not cause release of neurotransmitters from neurons innervating the one or more atrial vagal fat pad but does cause a change in properties of neurons innervating the one or more atrial vagal fat pad.

* * * * *